United States Patent [19]

Williams et al.

[11] Patent Number: 5,037,634

[45] Date of Patent: Aug. 6, 1991

[54] ORAL COMPOSITIONS CONTAINING STABILIZED COPPER

[75] Inventors: David R. Williams, Monroe; Alexander G. Ziemkiewicz, Shelton, both of Conn.

[73] Assignee: Chesebrough-Pond's USA Co., Division of Conopco, Inc., Greenwich, Conn.

[21] Appl. No.: 568,562

[22] Filed: Aug. 16, 1990

[51] Int. Cl.$^5$ .................. A61K 7/16; A61K 33/34
[52] U.S. Cl. ..................... 424/49; 424/54; 424/630
[58] Field of Search .................. 424/49, 630

[56] References Cited

U.S. PATENT DOCUMENTS

| | | | |
|---|---|---|---|
| 3,065,139 | 11/1962 | Ericsson et al. | 167/72 |
| 3,681,492 | 8/1972 | Kotzbauer | 424/141 |
| 3,937,804 | 2/1976 | Delaney et al. | 424/52 |
| 3,943,240 | 3/1976 | Delaney et al. | 424/49 |
| 4,160,022 | 7/1979 | Delaney et al. | 424/52 |
| 4,332,791 | 6/1982 | Raaf et al. | 424/52 |
| 4,487,757 | 12/1984 | Kiozpeoplou | 424/7.1 |
| 4,528,180 | 7/1985 | Schaeffer | 424/52 |
| 4,623,536 | 11/1986 | Winston et al. | 424/49 |
| 4,687,663 | 8/1987 | Schaeffer | 424/52 |
| 4,721,614 | 1/1988 | Winston et al. | 424/49 |
| 4,849,213 | 7/1989 | Schaeffer | 424/53 |
| 4,867,988 | 9/1989 | Chernack | 424/490 |
| 4,891,211 | 1/1990 | Winston | 424/49 |
| 4,943,429 | 7/1990 | Winston et al. | 424/49 |
| 4,980,154 | 12/1990 | Gordon | 424/53 |
| 4,983,379 | 1/1991 | Schaeffer | 424/52 |

FOREIGN PATENT DOCUMENTS 0011663 6/1980 European Pat. Off. .

OTHER PUBLICATIONS

"Stabilisation, Disinfection, Preservation", Textbook edited by S. S. Block (1983), Chapter 11, by F. J. Turner, pp. 240-250.
"Periodontics and Oral Hygiene", Keys, Jan. 1978, pp. 51-56.

Primary Examiner—Shep K. Rose
Attorney, Agent, or Firm—Milton L. Honig

[57] ABSTRACT

An oral composition is provided having exceptional anti-plaque action, the composition comprising a bicarbonate salt, a copper compound and a complexing agent to stabilize the copper.

16 Claims, No Drawings

ORAL COMPOSITIONS CONTAINING STABILIZED COPPER

BACKGROUND OF THE INVENTION

1. Field of the Invention

The invention relates to oral products for promoting health in the oral cavity.

2. The Related Art

Known oral products take the form of mouthwashes and dentifrices, the latter including paste and gel compositions. A variety of active agents have been used in such products to inhibit the growth of dental plaque which is composed of bacteria. Inhibition of dental plaque and its removal from teeth is not only cosmetically important, but is beneficial for prevention of dental caries, tartar formation and gingivitis.

Copper compounds have long been employed as antibacterial agents in oral products. U.S. Pat. No. 3,065,139 (Ericsson et al) reports a toothpaste comprising ascorbic acid, sodium percarbonate and a copper catalyst. U.S. Pat. No. 3,681,492 (Kotzbauer) also reports combinations of ascorbic acid with catalytic amounts of copper. Further improvements in the ascorbic acid/copper system have been disclosed in co-pending U.S. patent application Ser. No. 07/286,596 (Bird).

Formulating with copper is often difficult because of stability or bioavailability problems. U.S. Pat. No. 4,332,791 (Raaf et al) discloses that antimicrobial activity is seriously reduced where the abrasive is other than silica. Anti-plaque activity with a variety of metal ions, including copper, has reportedly been achieved by incorporation of tetradecylamine. See EP 0 011 663 (Ritchey).

Another substance which has been linked to oral health is that of sodium bicarbonate. Effectiveness of bicarbonate may be attributed to its abrasive character, but it also has been implicated in chemically inhibiting plaque, most often in coordination with hydrogen peroxide. The synergistic effect between hydrogen peroxide and bicarbonate has been widely promoted by Keyes through such articles as "Periodontics and Oral Hygiene", January 1987, pages 51–56.

U.S. Pat. No. 4,487,757 (Kiozpeoplou) discloses a toothpaste that physically segregates sodium bicarbonate from acidic ingredients to prevent contact therebetween prior to usage. U.S. Pat. No. 4,849,213, U.S. Pat. No. 4,687,663 and U.S. Pat. No. 4,528,180, all to Schaeffer, describe systems which house sodium bicarbonate separate from other components of the composition that may co-react therewith.

Based on our experiments and the known art, it is evident that oral compositions containing copper and/or sodium bicarbonate require special measures to ensure adequate storage stability and full bioavailability of actives when dispensed.

Accordingly, it is an object of the present invention to provide a bicarbonate and copper-containing oral composition that maintains stability of the bicarbonate and bioavailability of the copper even after prolonged storage.

This and other objects of the present invention will become more readily apparent upon consideration of the more detailed description and Examples which follow.

SUMMARY OF THE INVENTION

An oral composition is provided comprising:
(i) from about 0.5 to about 80% of a bicarbonate salt;
(ii) a copper compound present in an effective amount to inhibit bacterial growth; and
(iii) a complexing agent present in an effective amount to stabilize the copper compound.

DETAILED DESCRIPTION

Copper salts and sodium bicarbonate normally are unstable in the presence of one another. Instability is manifested by the precipitation of water insoluble material which is believed to be copper bicarbonate and/or copper hydroxide. Now it has been found that use of complexing agents in bicarbonate-copper formulations avoids precipitation and very significantly enhances the antibacterial effect. The antibacterial result may be due to the complexing agent interfering with precipitation of the copper, although this is merely a theory and the invention is not intended to be thereby limited.

Various types of complexing agents may be effective in the compositions of this invention. Most preferred, however, are those complexing agents with amine functionality which includes ammonia and organic amino compounds. Among the latter may be included $C_1$–$C_8$ mono-, di- and tri-alkylamines, of which the $C_1$–$C_4$ alkyl-type are particularly preferred because of water solubility, and the $C_1$–$C_8$ mono-, di- and tri-alkanolamines, of which the $C_1$–$C_4$ alkyl-type are also preferred. Illustrative of the complexing agents are triethylamine, diethylamine, triethanolamine, diethanolamine, and especially, ammonia in the form of ammonium hydroxide.

Amounts of the complexing agent may range from about 0.01 to about 20%, preferably between about 0.2 and 5%, optimally between about 1 and 2% by weight of the total oral composition.

Suitable copper compounds for the present invention are those which will supply copper ions and are toxicologically harmless, compatible with mucous membranes and, to some extent, water-soluble. Examples of suitable copper compounds are copper sulphate, copper halides and pseudohalides (such as copper chloride), copper nitrate, copper salts of carboxylic acids in the homologous series formic acid to decanoic acid, copper salts of polybasic acids in the series oxalic acid to suberic acid, and copper salts of hydroxycarboxylic acids, including glycolic, lactic, tartaric, malic and citric acids.

Further, specific examples include copper benzoate, copper gluconate, copper phytate, copper glycerophosphate, copper propionate, and copper salicylate.

The amount of copper, calculated as the metal, which may be included in compositions according to the present invention, ranges from about 1 ppm to 2000 ppm, preferably 100 to 300 ppm, more preferably 150 ppm to 250 ppm. On an overall weight basis, the copper compound may range in amount from 0.01 to 5%, preferably from 0.1 to 1.0%.

A third necessary component of formulations within the present invention is that of a bicarbonate salt. Advantageously, the bicarbonate will be the salt of an alkali metal, such as sodium or potassium. Normally, the bicarbonate is included in the composition in an amount sufficient to provide a neutral and basic pH when the composition is contacted with water, preferably a pH of from about 7.0 to about 9.5, most preferably about 8.0 to 9.0. The amount of bicarbonate actually employed can vary greatly depending upon the form of the composition and its intended method of application.

Typically, the concentration will range from about 0.5 to about 80%, preferably from about 5 to 50%, optimally between about 8 and 20% by weight of the total formulation.

Oral compositions of the present invention may be in the form of either a toothpaste or a mouthwash. Under certain preferred embodiments, the oral composition of the present invention may be dispensed in combination with a hydrogen peroxide-containing rinse or gel composition. With respect to the latter, the composition may include from 0.1 to 10% by weight of a peroxygen compound and, for the gel, an effective amount of a thickening agent in combination with water to gel the composition.

Beyond the essential ingredients of compositions of the invention, there will also be included traditional oral product components. A humectant and water system will normally be included. Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from about 25 to 99.9%, preferably from about 70 to 95% by weight. Particularly preferred is a liquid mixture of 3 to 30% water, 0 to 80% glycerol and 20 to 80% sorbitol.

When the oral compositions are in the form of a toothpaste or gel there will typically be included a natural or synthetic thickening agent in an amount from 0.1 to 10%, preferably about 0.5 to 5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive in addition to the bicarbonate. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range from about 5 to about 80% by weight.

Tartar control agents may be incorporated into compositions of this invention, especially effective will be agents containing phosphorous. Inorganic phosphorous tartar control agents may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tartar control agents include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from about 0.1 to 5% by weight.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers such as Gantrez S-97 ®, and anti-gingivitis actives.

The following examples will more fully illustrate the embodiments of this invention. All parts, percentages and proportions referred to herein and in the appended claims are by weight of the total composition unless otherwise stated.

EXAMPLE 1

A typical formulation of the present invention is a toothpaste whose composition is outlined in the Table below:

TABLE I

| Ingredient | Wt. % |
|---|---|
| PREMIX | |
| Polyol II (sorbitol and other sugars) | 38.1140 |
| Deionized water "A" | 4.0000 |
| Sodium saccharin | 0.5000 |
| Sodium fluoride | 0.4600 |
| Polyethylene glycol-32 | 5.0000 |
| Carboxymethyl cellulose gum | 0.8000 |
| Deionized water "B" | 5.3080 |
| Ammonia | 1.3080 |
| Copper sulphate 5-hydrate | 0.1600 |
| BASE PASTE | |
| Sodium bicarbonate, coarse granular | 15.0000 |
| Sylox 15X (thickening silica) | 4.2500 |
| Syloid 63XX (abrasive silica) | 7.5000 |
| Titanium dioxide | 0.3000 |
| FLAVOR PACKAGE | |
| Polyol II | 9.1830 |
| Sodium lauryl sulphate | 2.9790 |
| SDA 38B alcohol | 2.8380 |
| Flavor | 1.9000 |
| Menthol | 0.6000 |
| Color | 0.0050 |
| Total | 100.7000 |

EXAMPLE 2

The relative antiplaque activities of toothpaste formulations essentially similar to those of Example 1 have been assessed using a 48-hour plaque screening model. Studies were conducted in a double blind manner, with neither examiner nor panelists having knowledge of the product identity. Panelists were required to meet certain entrance criteria in order to be included in the study.

Panelists received a full mouth supragingival prophy and scaling. Panelists were then instructed to refrain from all oral hygiene measures, except use of assigned test products, for the next 48 hours. Treatments were performed twice a day, in the morning (supervised) and in the evening, for two days. The following day the panelists used a disclosing solution and were then examined for plaque on the Ramford teeth using the DMPI plaque scoring system.

Treatments were prepared as follows: Panelists using Crest (Control) used 15 milliliters of a 25% toothpaste slurry for each treatment. All copper sulfate treatments were in combination with a hydrogen peroxide rinse or peroxide gel slurry. For the baking soda/copper and peroxide treatments, separate 25% slurries of sodium bicarbonate/copper paste and peroxide gel were prepared. Panelists used 15 milliliters of a 1:1 mixture of these two slurries for each treatment, with the two phases being mixed just prior to use. Treatment slurries were prepared fresh daily.

TABLE II

| Test No.* | Description | % Plaque Reduction |
|---|---|---|
| 1 | Copper Sulfate without abrasives | 31.0 |
| 2 | Copper Sulfate in Bicarbonate/Silica System | 0.0 |
| 3 | Copper Sulfate in Bicarbonate/Silica/IMP System | 1.0 |
| 4 | Copper Sulfate in Bicarbonate/IMP System | 1.8 |
| 5 | Copper Sulfate stabilized with Ammonia in a Bicarbonate/Silica System | 33.0 |

*All formulas delivered the equivalent of 200 ppm copper as toothpaste.

Table II presents results of the 48-hour plaque evaluation. The first four tests illustrate the inactivation of Copper by abrasive systems. Test 5 clearly indicates enhanced plaque reduction using ammonia stabilized Copper in the presence of abrasives.

The foregoing description and Examples illustrate selected embodiments of the present invention. In light thereof, various modifications will be suggested to one skilled in the art, all of which are within the spirit and purview of this invention.

What is claimed is:

1. An aqueous oral hygiene toothpaste, gel, mouthwash or rinse composition comprising:
   (i) from about 0.5 to about 80% of a bicarbonate salt;
   (ii) a copper compound present in an amount to provide from about 1 to about 2000 ppm copper calculated as copper metal; and
   (iii) a complexing agent present in an amount from about 0.01 to about 20% by weight, said complexing agent being selected from the group consisting of ammonia, alkylamines and alkanolamines.

2. An oral composition according to claim 1, wherein said complexing agent is an alkanolamine.

3. An oral composition according to claim 1, wherein the complexing agent is ammonia.

4. An oral composition according to claim 1, wherein the amount of bicarbonate ranges from 8 to 20% by weight.

5. An oral composition according to claim 1, wherein the bicarbonate salt is selected from the group consisting of sodium bicarbonate, potassium bicarbonate and mixtures thereof.

6. An oral composition according to claim 1, wherein the copper compound is selected from the group consisting of copper sulphate, copper chloride and copper bromide.

7. An oral composition according to claim 1, wherein the composition is in toothpaste form.

8. An oral composition according to claim 1, wherein the composition is in mouthwash form.

9. A method for reducing plaque on teeth in an oral cavity comprising contacting said teeth with a toothpaste, gel, mouthwash or rinse composition comprising from about 0.5 to about 80% bicarbonate salt, from about 1 to about 2000 ppm calculated as copper metal of a copper compound and from about 0.01 to about 20% by weight of a complexing agent which is selected from the group consisting of ammonia, alkylamines and alkanolamines.

10. A method according to claim 9, wherein said complexing agent is an alkanolamine.

11. A method according to claim 9, wherein the complexing agent is ammonia.

12. A method according to claim 9, wherein the amount of bicarbonate ranges from 8 to 20% by weight.

13. A method according to claim 9, wherein the bicarbonate salt is selected from the group consisting of sodium bicarbonate, potassium bicarbonate and mixtures thereof.

14. A method according to claim 9, wherein the copper compound is selected from the group consisting of copper sulphate, copper chloride and copper bromide.

15. A method according to claim 9, wherein the composition is in toothpaste form.

16. A method according to claim 9, wherein the composition is in mouthwash form.

* * * * *